United States Patent [19]

Mullen

[11] 4,035,478

[45] July 12, 1977

[54] CLEAR, WATER-WHITE HAIR CONDITIONING COMPOSITION

[75] Inventor: Patricia Mullen, Flushing, N.Y.

[73] Assignee: American Cyanamid Company, Stamford, Conn.

[21] Appl. No.: 664,469

[22] Filed: Mar. 8, 1976

[51] Int. Cl.$^2$ .......................................... A61K 7/08
[52] U.S. Cl. ............................ 424/70; 252/DIG. 2; 252/DIG. 3; 424/DIG. 2; 424/78; 424/81
[58] Field of Search ................ 424/70, DIG. 2, 78, 424/81; 252/DIG. 2, DIG. 3, DIG. 13

[56] References Cited

U.S. PATENT DOCUMENTS

| | | | |
|---|---|---|---|
| 2,950,255 | 8/1960 | Goff | 424/70 X |
| 3,423,504 | 1/1969 | Birkelo et al. | 424/70 |
| 3,577,528 | 5/1971 | McDonough et al. | 424/70 |
| 3,910,862 | 10/1975 | Barabas et al. | 424/71 X |
| 3,914,403 | 10/1975 | Valan | 424/70 X |
| 3,980,769 | 9/1976 | Ghilardi et al. | 424/70 |
| B 438,048 | 3/1976 | Fogel et al. | 424/70 |

*Primary Examiner*—Frederick E. Waddell
*Assistant Examiner*—Vera C. Clarke
*Attorney, Agent, or Firm*—Charles J. Fickey

[57] ABSTRACT

Hair conditioning composition for application following shampooing, to give the hair better manageability and appearance. The composition is essentially water white and comprises a high molecular weight copolymer of vinylpyrrolidone and dimethylaminoethylmethacrylate quaternized with diethylsulfate or dimethylsulfate in combination with oleyl dimethylbenzylammonium chloride.

5 Claims, No Drawings

CLEAR, WATER-WHITE HAIR CONDITIONING COMPOSITION

BACKGROUND OF THE INVENTION

This invention relates to a clear hair conditioning composition for application following shampooing. More particularly, it relates to a clear, essentially aqueous, water-white hair conditioning composition having excellent conditioning properties and stability at low temperatures.

Rinses typically are preparations which are applied to wet hair following shampooing and then rinsed out with clear water before the hair is set and dried. For many years an acid consisting of lemon juice or vinegar in water was considered an essential finishing touch to shampooing in order to remove residual soap film. Many proprietary products served this same function. With the advent of surfactant-based shampoos and improvement of soap shampoos, this type of rinse has fallen into disuse.

Three types of after shampoo rinses find reasonably widespread use today: creme rinses, dandruff rinses and hair coloring rinses.

Creme rinses are used after shampooing to give the hair a better finish, particularly with respect to softness and lubricity. They are particularly effective in eliminating snarling and improving wet combability. Almost without exception, creme rinses are based on quarternary ammonium compounds substantive to the hair. The quaternary ammonium compounds are effective antistatic agents and tend to reduce friction on wet hair. Typically, a creme rinse is a viscous, opaque liquid concentrate, which may be pearly in appearance. The active quaternary ammonium compounds in most creme rinses is stearyldimethylbenzylammonium chloride; another common use is distearyldimethylammonium chloride.

In a similar manner, in recent years considerable effort has been directed toward developing creme rinse shampoos. These shampoos containing cationic resins or nonionic materials of low solubility in anionic-amphoteric surfactant systems. Several synthetic polymers have been used in creme rinse shampoo compositions, including Polymer JR (Union Carbide), a polymer of hydroxyethylcellulose reacted with epchlorohydrin and quaternized with triethylamine, and Gafquat Quaternary Polymers (quaternized vinypyrrolidone copolymers), available from GAF Corporation.

Present day trends toward more natural hair styles has created a need for a conditioning agent which need not be rinsed from the hair following application as is required with conventional creme rinses. The requirements for such a conditioning agent are that it must be a clear, water-white, essentially aqueous solution which can be applied to the hair following shampooing without rinsing and which provides softness, fly-away control and body to dry hair and manageability to both wet and dry hair, such as wet combability, freedom from snarls and lubricity. In addition the conditioning agent must not leave a residual film on the hair, perceived as an unnatural feel.

Certain cationic high molecular weight (1,000,000) copolymers of vinylpyrrolidone and dimethylaminoethylmethacrylate quaternized with dimethysulfate or diethysulfate are soluble in water and provide excellent conditioning action when used in combination with stearyldimethylbenzyl ammonium chloride. However, it was discovered that stearyldimethylbenzyl ammonium chloride exchanged with the polymer in solution, causing insoluble steryldimethylbenzylammonium sulfate to precipitate on standing and producing an undesirable and unacceptable haziness in the clear rinse composition, particularly at low temperatures, such as encountered in the winter, for example, 5° C to −10° C.

Of many compounds investigated to find a replacement for stearyldimethylbenzylammonium chloride which did not exchange with the polymer, one, oleyl dimethylbenzyl-ammonium chloride, provided clear, water-white aqueous solutions. It does not appear to interact or exchange with the polymer to produce an insoluble precipitate, Moreover, oleyl dimethylbenzylammonium chloride provided excellent conditioning (anti-static) properties equal to solutions containing stearyldimethylbenzylammonium chloride. Additionally, the clear rinses are stable at the aforementioned low temperatures.

SUMMARY OF THE INVENTION

The present invention is based on the discovery of a clear, essentially aqueous water-white, stable hair conditioning rinse comprising a high molecular weight copolymer of vinyl pyrrolidone and dimethylaminoethylmethacrylate quaternized with diethylsulfate or dimethylsufate in combination, in solution, with oleyl dimethylbenzylammonium chloride.

The compositions of the present invention consist essentially of aqueous solutions of the aforementioned cationic vinyl pyrrolidone copolymers and oleyl dimethylbenzyl-ammonium chloride. Ordinarily, the compositions will contain additional additives, such as a preservative and a fragrance, although these are optional. Small amounts of alcohol may be included to carry some fragrances into solution, and the alcohol may be used in amounts up to 20%. The compositions may contain additional body builders, such as certain Cartex polymers (National Starch), amine salts of an aminoethyethylacrylate phosphate/acrylate copolymer.

The vinyl pyrrolidone copolymers useful in the present invention are described in detail in GAF German Offenlegundscrift No. 2,103,899, published Aug. 5, 1971. They conform to the polymeric structure:

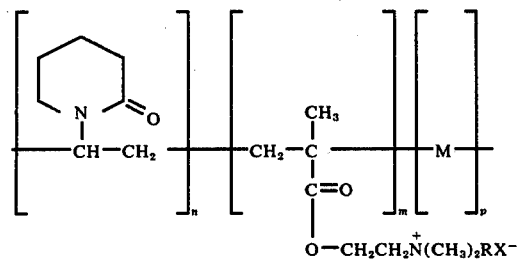

M is a vinyl monomer copolymerizable with vinylpyrrolidone, R is methyl or ethyl, and X is $CH_3SO_4^-$ or $C_2H_5SO_4^-$; n is 40–90 mole percent, m is 5–40 mole percent, and p is 0–50 mole percent.

Preferred copolymers within the above class are high molecular weight (about 1,000,000) and contain 70–90 mole percent vinylpyrrolidone and 10–30 mole percent dimethyl-aminoethylmethacrylate quaternized with dimethyl- or diethyl-sulfate. However, copolymers similar to these may contain minor amounts of a monomer (M) without departing from the scope of the invention. Such comonomers may include methyl vinyl ether, methylmethacrylate, styrene, vinylacetate, vinylchloride, vinylidine chloride, methacrylonitrile, etc.

The vinylpyrrolidone polymers are used in the compositions of the invention in an amount ranging from 0.2 to 0.6 weight percent (real basis).

The oleyldimethylbenzylammonium chloride is used in the compositions in an amount from about 0.2 to 0.6 weight percent (real basis).

The pH of the compositions of the invention are adjusted to the range pH 3 4, e.g., by the addition of lactic acid if necessary.

The following examples further illustrate the invention.

EXAMPLE 1

A clear rinse formulation for dry and/or damaged hair prepared containing the following:

| | Parts by Weight (real basis) |
|---|---|
| Vinylpyrrolidone copolymer* (20% aqueous solution) | 0.6 |
| Aminoethylacrylate phosphate copolymer** (18% aqueous solution) | 0.3 |
| Oleyldimethylbenzylammonium chloride (50% active) | 0.4 |
| 2-Bromo-2-nitropropane-1,3-diol | 0.05 |
| Fragrance | 0.15 |
| Deionized water | q.s. to 100 |

*90/10 Copolymer of vinylpyrrolidone and dimethylaminoethylmethacrylate quanterized with diethylsulfate
**Catrex Polymer, described as an aminoethylacrylate phosphate/acrylate, amine salt; National Starch & Chemical Co.

EXAMPLE 2

A clear rinse formulation for normal hair was prepared as follows:

| | Parts by Weight (real basis) |
|---|---|
| Vinylpyrrolidone copolymer of Ex. 1 | 0.4 |
| Aminoethylacrylate phosphate copolymer of Ex. 1 | 0.2 |
| Oleyldimethylbenzylammonium chloride (50% active) | 0.4 |
| 2-Bromo-2-nitropropane-1,3-diol | 0.05 |
| Fragrance | 0.1 |
| Deionized water | q.s to 100 |

EXAMPLE 3

A clear rinse formulation useful for oily hair was prepared as follows:

| | Parts by Weight (real basis) |
|---|---|
| Vinylpyrrolidone copolymer of Ex. 1 | 0.3 |
| Oleylidimethylbenzylammonium Chloride (50% active) | 0.2 |
| Ethanol | 20.0 |
| 2-Bromo-2-Nitropropane-1,3-diol | 0.05 |
| Fragrance | 0.1 |
| Deionized water | q.s. to 100 |

EXAMPLE 4

Example 2 was repeated using a vinylpyrrolidone copolymer containing 80 mole percent vinylpyrrolidone and 20 mole percent dimethylaminoethylmethacrylate quaternized with diethysulfate to prepare a clear rinse composition.

EXAMPLE 5

When Example 3 was repeated using stearyl dimethylbenzylammonium chloride instead of oleyl dimethylbenzylammonium chloride a haze formed on standing. The precipitate was found to be stearyldimethylbenzylammonium sulfate.

I claim:

1. A clear, water-white hair rinse composition comprising an essentially aqueous solution of 1. from about 0.2 to 0.6 percent a vinylpyrrolidone compolymer having the structure:

$$\left[ -CH_2-CH- \underset{\underset{O}{\overset{\displaystyle N}{|}}}{\bigcirc} \right]_m \left[ -CH_2-CH- \underset{\underset{CH_2CH_2\overset{+}{N}(CH_3)\ R\ X^-}{\overset{\displaystyle |}{\underset{\displaystyle |}{\overset{\displaystyle C=O}{|}}}}}{} \right]_n$$

where $m$ is 70–90 mole percent, $n$ is 10–30 mole percent, R is methyl or ethyl and X is $CH_3SO_4^-$ or $C_2H_5SO_4^-$ and 2. from about 0.2 to 0.6 percent oleyldimethylbenzylammonium chloride, based on the weight of said composition.

2. The composition of claim 1 wherein R is ethyl, X is $C_2H_5SO_4^-$ and the polymer molecular weight is about 1,000,000.

3. The composition of claim 1 wherein the composition contains from about 0.2 to 0.6 percent of the vinylpyrrolidone copolymer and from about 0.2 to 0.4 percent oleyldimethylbenzylammonium chloride.

4. The composition of claim 1 having a pH of about 3 to 4.

5. The composition of claim 1 also containing lactic acid.

* * * * *